United States Patent [19]

Piccone et al.

[11] Patent Number: 4,566,464
[45] Date of Patent: Jan. 28, 1986

[54] IMPLANTABLE EPILEPSY MONITOR APPARATUS

[76] Inventors: Vincent A. Piccone; John N. Piccone; Louis A. Piccone, all of 377 Gansvoort Blvd., Staten Island, N.Y. 10314; Robert F. LeVeen, 312 Lombard St., Philadelphia, Pa. 19147; Eric G. LeVeen, 3-3 Woodlake Rd., Albany, N.Y. 12200

[21] Appl. No.: 286,851

[22] Filed: Jul. 27, 1981

[51] Int. Cl.$^4$ ............................................. A61B 5/04
[52] U.S. Cl. ..................................... 128/732; 128/731
[58] Field of Search ......... 128/731, 732, 903, 419 PG

[56] References Cited

U.S. PATENT DOCUMENTS

| | | | |
|---|---|---|---|
| 3,724,455 | 4/1973 | Unger | 128/903 |
| 3,832,994 | 9/1974 | Bicher et al. | 128/903 |
| 3,833,005 | 9/1974 | Wingrove | 128/419 PG |
| 3,837,339 | 9/1974 | Aisenberg et al. | 128/903 |
| 3,863,625 | 2/1975 | Viglione et al. | 128/732 |
| 4,214,591 | 7/1980 | Sato et al. | 128/731 |
| 4,312,354 | 1/1982 | Walters | 128/419 PG |

Primary Examiner—Kyle L. Howell
Assistant Examiner—Mitchell J. Shein
Attorney, Agent, or Firm—Gipple & Hale

[57] ABSTRACT

A low-power personal epilepsy seizure warning system is disclosed based on the clinical observation that while the brain potentials marking the onset of epilepsy vary from patient to patient, indicative brain potentials in any one patient are highly likely to remain constant. The system includes an implantable monitor to detect brain potentials and recognize the onset of a seizure, and an external warning unit to warn the patient when a seizure is imminent. The monitor is configured to recognize a patient's indicative potentials after preoperative EEG observation, and may include relatively simple analog circuitry to recognize simple forms, or a microprocessor and programmed memory to recognize complex forms utilizing algorithms such as the fast Fourier transform. An external program adjustment unit may also be utilized to increase or decrease the sensitivity of the monitor corresponding to the patient's experience of insufficient or excessive warnings after implantation. Since the implanted monitor uses high power for transmission only during warnings or sensitivity adjustment, its overall consumption of power is low and it may be expected to operate without the need for replacement over a period of several years.

4 Claims, 3 Drawing Figures

IMPLANTABLE EPILEPSY MONITOR APPARATUS

BACKGROUND OF THE INVENTION

The present invention generally relates to epilepsy therapy and more specifically to an implantable seizure detection and warning apparatus for epileptic patients.

Epilepsy is a condition characterized by recurrent seizures of various types associated with disturbances of consciousness. The incidence of epilepsy has been estimated at one of every two hundred to three hundred of the population. In the United States, the number of cases exceeds two hundred and fifty thousand individuals.

A variety of seizure types have been recognized including grand mal seizures, petit mal seizures, psychomotor seizures, Jacksonian seizures and focal seizures. A seizure may or may not follow warning symptoms detectable to the patient. Major attacks begin with a sudden loss of consciousness. As the attack continues to develop, all voluntary muscles go into severe spasm, breathing ceases, the patient's skin turns blue, and life seems almost at an end. The patient then suddenly becomes totally relaxed and muscle spasms are replaced by jerking or clonic uncontrolled motions of increasing strength. Finally, the spasms cease altogether and consciousness gradually returns.

A seizure may appear to occur spontaneously, without external stimuli, although in many patients a stimulus such as flashing lights, repetitive sounds or stressful situations are easily identified as the trigger of the seizure. While seizures often occur during sleep, a seizure during waking hours may cause the patient to injure himself when consciousness is suddenly lost. The danger posed to the epileptic patient and others is obvious. He may fall and strike his head, fall into moving machinery or lose control of an automobile.

The recent decades have seen a real increase in the inclusion of epileptic patients in family life, social activities and business. Medical treatment can control seizures in about seventy-five percent of epileptic patients, but each patient must minimize exposure to many inherently dangerous situations commonly encountered in a modern industrial society. Obtaining a driver's license for a patient remains a difficulty, and the knowledge of the possibility of unexpected attacks causes chronic anxiety in many patients.

Internally, the onset of a seizure is reflected in a marked departure of brain potential from the normal form. The characteristic feature of the normal adult electroencephalogram (EEG) is an Alpha rhythm in a frequency range of eight to twelve hertz at a potential measured in the microvolt range. An example of a normal adult waking state EEG tracing is illustrated in FIG. 1.

Higher voltage processes of unique form are intimately linked with seizures and are called paroxysmal. A typical paroxysmal waveform is illustrated in FIG. 2. These waves may arise in a single focal area of the brain and spread gradually to other areas, or instead rapidly involve all cerebral areas, and the type of waveform exhibited will also vary from patient to patient. However, in any one patient it is highly likely that the EEG waveform and propagation pattern at seizure onset will repeat the pattern of prior seizures. While other disease states such as migraine, narcolepsy and vertigo involve high voltage EEG patterns, so that the pattern alone is not uniquely diagnostic of epilepsy, the EEG spikes of epilepsy are useful documentation of the disease during seizures. The high voltage waveform is infrequent and less numerous in the interictal period of epileptic patients and is then a particularly important diagnostic tool. A changing frequency of transient spikes may be related to changes in the severity of the disease, and has been used to assess the effectiveness of drug therapy.

The analysis of EEG sharp transients according to frequency and configuration continues to hold promise as the method for evaluating epileptic patients in response to drug control of epilepsy.

Standard EEG procedures utilize electrodes applied to the scalp and coupled to systems employed to measure and record the electropotential changes associated with normal and abnormal cerebral activity. The patient is typically connected directly by wires to the system, and must lie motionless during a period of approximately twenty minutes to complete the study. This technique incorporates some substantial limitations. The very short time of study of the patient may not include abnormal EEG activity. The patient is isolated from normal daily activity which may include seizure stimuli. Furthermore, any type of muscle activity, including movements of the eye, produces strong aberrations in the EEG tracing. Moreover, observer analysis and interpretation of EEG tracings remains more an art than a science with the possibility for wide disagreement between observers of an EEG.

Radiotelemetry systems designed to monitor the EEG potentials remotely were developed late in the 1940's. Electrodes applied to the scalp were coupled to a portable transmitter unit worn by the patient. The radio signals were then received by a remote receiver and converted to a tracing displayed on a oscilloscope or paper. Such developments offered an opportunity to monitor epileptic patients in something akin to a daily routine over an extended period of time. A therapy plan could then include a quantitative correlation of seizures and EEG activity in evaluating the efficacy of antiepileptic drugs.

Initially, EEG telemetry units of practical size and mass were of low power, restricting the monitored patient to a small area within range of the telemetry receiver. However, advancements in solid state electronics technology gave rise to more powerful transmitters and by 1973, nine manufacturers were offering EEG telemetry equipment. Two channel, three channel and sixteen channel transmitters were made available for simultaneous monitoring of separate areas of the brain. These systems experienced external interference on AM channels by sources such as motors and fluorescent lights and, on FM channels, by commercial FM stations.

Other developments have improved the usefulness of portable EEG monitoring systems. A portable cassette EEG recorder was demonstrated in 1975, and has been improved to include four channel recording capability. While the cassette recorder adds somewhat to the burden carried by the patient and prohibits correlation with patient activities, it does allow capture of data away from receivers in the patient's normal environment and without interference. The development of economical video recording systems have allowed simultaneous EEG and video monitoring to correlate external patient symptoms with EEG changes, although this system also involves restraining the patient to an area close by a video camera. Band pass filters have been successfully developed to minimize interference from muscle potentials. An induction-powered, implanted EEG transmitter has also been introduced.

Development of EEG analysis systems has lagged behind the advances in EEG data capture and transmission systems. The techniques used to analyze EEG data from epileptic patients generally require the use of a digital computer. The size, mass and power requirements of such a computer have heretofore implied a stationary computer and a patient within transmission distance of the computer. Despite these inadequacies, computer analysis of EEG data is now entering clinical use, and remains an area of intense study.

Analysis techniques under scrutiny include matched filtering, also known as "template matching", time-averaged running correlation coefficients analysis, and fast Fourier analysis of component frequencies. EEG sharp transient detection and quantification has received great attention because transients are one of the more important features in the EEG tracings of epileptic patients. A representative system is one which detects brain waves with a second derivative exceeding the average second derivative of the preceding wave by more than a specified threshold mount. This system can act as a smart sensor of sharp transients, and notify a diagnostician to examine the tracings more closely. Template matching techniques can detect a specific waveform quite dependably, but departures from the waveform template are not detected at all. Computation of a running correlation coefficient between two EEG channels has the potential of signalling a change in the EEG, provided that only one channel changes.

The development of the fast Fourier transform algorithm for digital spectral analysis offers accurate and flexible recognition of various waveforms. However, the use of Fourier analysis has heretofore been limited, like the aforementioned analysis techniques, to relatively powerful and stationary computer systems.

SUMMARY OF THE INVENTION

The present inventive system comprises an implantable, internally powered seizure monitor unit for analysis of EEG patterns and an unobtrusive external warning unit to inform the patient of seizure onset as detected by the unit.

The characteristic seizure waveform of the patient is determined by extended preoperative EEG monitoring, and the internal unit is then configured by hardware or software means to detect appropriate EEG activity and communicate with the warning unit by radio transmission. An external program adjustment device is also provided, packaged either with the warning unit or as a separate component, and may be used to increase or decrease the sensitivity of the monitor unit on the basis of postoperative experience. The program adjustment device can communicate with the monitor unit by radio transmission also.

The monitor unit combines monitoring and analysis of EEG patterns in a lightweight, compact package which provides realtime patient status alerts while freeing the patient from the need to remain in transmission range of a stationary computer.

These and other objects and advantages of the invention will become more readily apparent when referring to the following detailed description thereof in conjunction with the accompanying drawings.

DETAILED DESCRIPTION OF THE DRAWINGS

Figure 3:
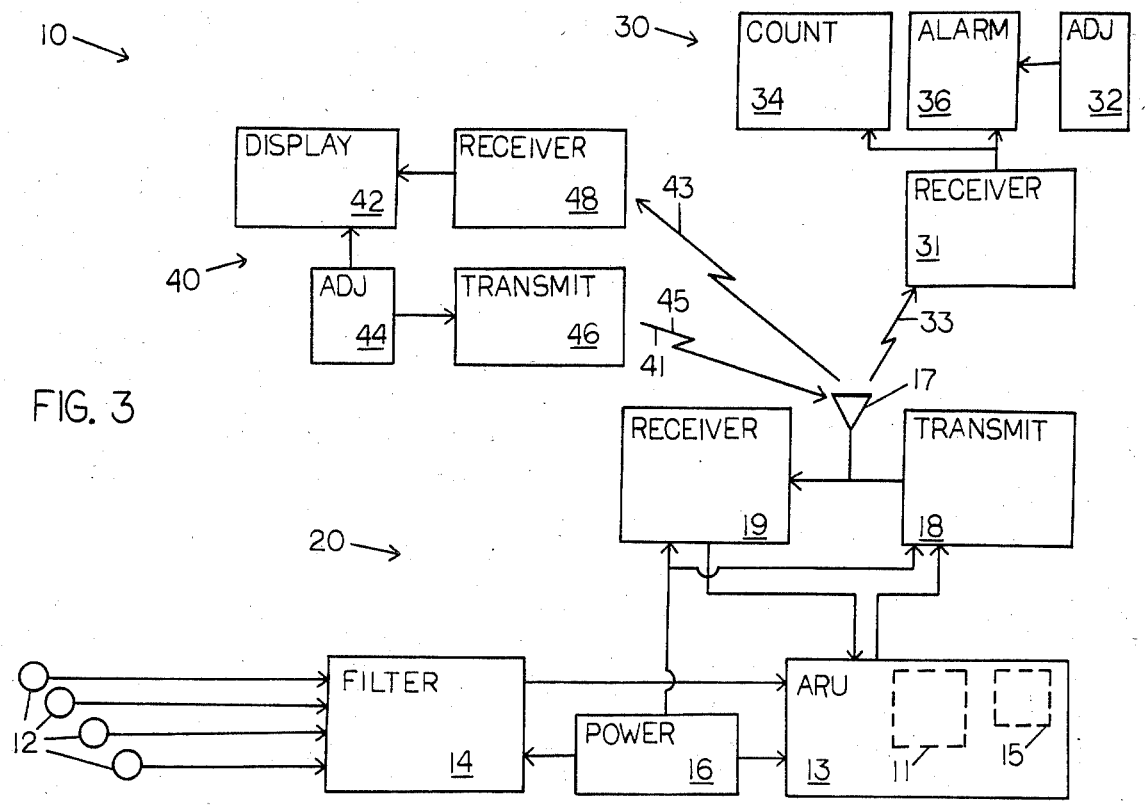
FIG. 3 is a block diagram of an implantable monitor, warning receiver, and program transceiver according to the present invention.
Figure 1:
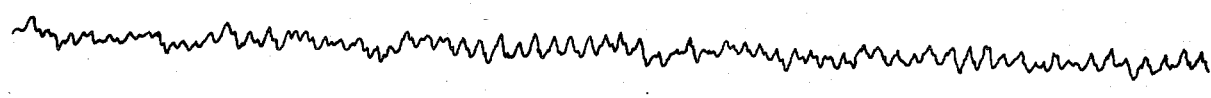
FIG. 1 is an electroencephalograph tracing of typical brain potentials in a normal waking state.
Figure 2:
FIG. 2 is an electroencephalograph tracing of typical brain potentials in a grand mal seizure state.

The best mode and preferred embodiment of the present inventive system is illustrated in FIG. 3 and is generally indicated at 10. The system 10 comprises a monitor 20 implanted within the body, a warning receiver 30 and a program transceiver 40 carried on the person of the epileptic patient. Warning receiver 30 and program transceiver 40 may be advantageously housed together in a single enclosure or housing.

The monitor 20 is preferably a hermetically sealed, internally powered device which is implanted subcutaneously over the upper part of the anterior aspect of the chest. The monitor 20 comprises a plurality of sensing electrodes 12, filter 14, an analytic-recognition unit (ARU) 13, power supply 16, radio-frequency transmitter 18, radio-frequency receiver 19 and antenna 17. The electrodes 12 may be of any well known state-of-the-art subcutaneous EEG type implanted directly over the most opportune areas of the cerebral cortex as determined by preoperative EEG observation. The single most opportune area in most patients has been found to be the temporal area.

A typical electrode may consist of a conductive non-corrosive plate, helical wire surrounded by silicone rubber insulation, and a filter connector pin. The lead of each electrode 12 is then brought through a subcutaneous tunnel down along the side of the neck and into the anterior aspect of the chest, where the electrodes are multiplexed (if necessary) and coupled and sealed to a standard state-of-the-art filter 14. The filter 14 is configured as is well known in the art to block potentials generated by muscle movement and transmit other potentials. The output of filter 14 is in turn coupled to ARU 13.

The ARU is configured to analyze received potentials for those gross abnormalities typical of premonitory or seizure activity. The sensitivity and recognition parameters of ARU 13 used in any one patient are chosen so as to conform to the waveform detection goals in that patient's particular type of epilepsy. The more complex problems typically require a microprocessor 11 in the ARU 13 when the period, amplitude and phase relationships within a waveform must be analyzed. Coupled to the microprocessor 11 which can be a 6502 or eight-bit processor is a memory 15, containing both an analysis program and scratchpad memory area for use by the program. Less complex waveform analysis can be alternatively accomplished without the use of microprocessor 11 and memory 15 by resorting to well known analog waveform detection circuitry.

The ARU 13 is coupled to radio-frequency transmitter 18 and radio-frequency receiver 19. Both the transmitter 18 and receiver 19 are coupled to antenna 17. When the ARU 13 determines from analysis of brainwave forms detected through electrodes 12 that a seizure is imminent, ARU 13 causes transmitter 18 to transmit a coded signal on a frequency compatible with warning receiver 30. Warning receiver 30 then produces an alarm detectable by the patient in any well known fashion, such as an audible buzz.

The ARU 13 is configured so as to allow adjustment of its sensitivity and recognition parameters which are initially set according to preoperative EEG observation as described above. The program transceiver 40 is provided to communicate with ARU 13 through transmitter 18 and receiver 19 so as to determine the sensitivity and recognition parameters of ARU 13 and adjust the sensitivity and recognition parameters according to the patient's experience with excessive false alarms or inadequate warning prior to seizures. Additionally, transceiver 40 may be advantageously used to increase the sensitivity of ARU 13 when detection of maximal amounts of abnormal EEG activity, including subclinical waveform discharges, are needed to determine optimal dosages of therapeutic drugs. Program transceiver 40 is configured to transmit an initial query to receiver 19 whereupon ARU 13 transmits information indicating the sensitivity setting through transmitter 18 to transceiver 40. For these purposes, it may be advantageous to configure transmitter 18 so as to transmit information on a frequency distinct from that on which warnings are transmitted and to configure receiver 19 to receive on yet a third frequency. Whatever frequencies are chosen for these communications, receivers 30 and transceiver 40 must have their frequencies of operation adjusted accordingly to facilitate communication.

Monitor 20 may be powered by an appropriate power source such as a long-life battery, isotopic thermocoupled or power receiver coupled inductively to an external power transmitter. A lithium battery is one type of long-life battery which is well known for use with implanted electronic devices. The monitor 20 generally consumes very low power except during periods of transmission, in contrast to prior art continuous telemetry devices.

The warning receiver 30 may include warning receiver 31, alarm 36, alarm volume adjustment means 32 and a resettable counter 34. Receiver 31 receives warning signal 33 from transmitter 18 and increments counter 34 as well as activating alarm 36. The counter 34 may be adapted to count the number of warnings received, and may be reset at the end of a statistical period, such a a day. Receiver 30 may typically be compact enough to be worn in a shirt pocket placed directly over the implanted monitor 20 and powered by a rechargeble battery. Alternately, receiver 30 can be configured as a bedside unit, powered by wall current, including a radio-frequency receiver of increased sensitivity and a directional antenna. Thus, the patient could place the receiver 30 a short distance away beside a bed while sleeping rather than be forced to wear receiver 30 constantly.

Program transceiver 40 may include display means 42 for displaying to the patient a numerical quantification of the sensitivity and recognition parameters indicated by the ARU 13 when queried by transceiver 40. The transceiver 40 also includes adjustment means 44 to adjust the quantities displayed on display means 42. When transceiver 40 is activated by the user, program transmitter 46 signals a query 41 to monitor 20 which returns sensitivity and recognition parameter data signal 43 through program receiver 48 to display 42. The user may also use adjustment means 44 to transmit an adjusted data signal 45 to monitor 20.

In operation of the present invention, the implantable monitor is first adjusted to detect the patient's characteristic EEG patterns at the onset of a seizure and the monitor is sealed and implanted in any manner well known in the art of surgical implantation of electronic devices. The monitor 20 immediately begins monitoring the EEG patterns of the patient, a task which by itself consumes low power. From time to time, the onset of a seizure will be detected by monitor 20, and a warning signal will then be transmitted to warning unit 30 by monitor 20. As noted above, warning unit 30 is typically worn on the person of the patient, preferably in a shirt pocket near the implant site. The patient typically is warned by warning unit 30 prior to experiencing any detectable physical symptoms of the onset of a seizure. At this time, warning unit 30 also increments counter 34. The patient may adjust the volume level of the alarm sounded by warning unit 30 by manipulation of adjustment means 32, and the patient typically will take steps to avoid the seizure stimuli, if known, or remove himself from danger should consciousness be lost.

After an interval of experience with monitor 20 and warning unit 30 the patient may find that monitor 20 is too sensitive and produces warnings when in fact a seizure is not imminent. Alternatively, the patient may find that the monitor 20 is not sensitive enough, and some seizure episodes are not reported to the patient in advance. In either instance, the patient may utilize program transceiver 40 to adjust the sensitivity and recognition parameters of the monitor 20 accordingly.

Program transceiver 40 is a power-consuming device due to use of display means 42 and transmitter 46. Since monitor 20 does not require frequent adjustment, program transceiver 40 is normally inactive. When activated, transmitter 46 queries the present sentivity and recognition parameters of ARU 13 with a query signal 41. A data signal 43 is returned from monitor 20 and received by program receiver 48. This information is then displayed on display means 42. The user may adjust the displayed factors according to his or her experience by manipulating adjustment means 44 which changes the information displayed and causes transmitter 46 to transmit an adjusted data signal 45 to monitor 20. Upon reception of an adjusted data signal 45, ARU 13 adjusts its sensitivity and recognition parameters accordingly.

It can be seen that the present inventive system offers continuous monitoring of epileptic cerebral activity and reporting thereof to the patient in a form which is understandable and personally useful. Warning signals provided by the inventive system can inform the patient of the need to change medication dosage, to avoid causitive stimuli if known, to avoid dangerous stairways, machinery, automobile traffic and other situations potentially harmful to the patient and others, and to seek help when necessary. The warning sound of the warning receiver 30 can also attract aid to an isolated unconscious epileptic patient.

It should be apparent that while there has been described what is presently considered to be a preferred form of the inventive system in accordance with the Patent Statutes, changes may be made in the disclosed embodiment without departing from the true spirit and scope of the invention as expressed in the following claims.

What is claimed is:

1. A personal epilepsy seizure warning system comprising an implantable monitor meand adaptable to detect brain potentials indicating the onset of an epileptic seizure at a predetermined sensitivity level, said monitor means further comprising means to transmit an alarm signal when said brain potentials indicating an epileptic seizure are detected, and an external warning means adapted to receive said alarm signal and notify the patient when said alarm signal is received, and further including external program transceiver means adapted to adjust said predetermined sensitivity level.

2. The apparatus as claimed in claim 1 wherein said external warning means comprises a small housing adapted to be worn by the user, said housing containing warning receiver means adapted to receive alarm signals and alarm means adapted to notify the patient when alarm signals are received.

3. A personal epilepsy seizure warning system comprising implantable monitor means adapted to detect brain potentials indicating onset of an epileptic seizure and external warning means adapted to notify a patient of onset of an epileptic seizure; said implantable monitor means comprising sensing means adapted to detect brain potentials from at least one area of the brain, single-input filter means connected to said sensing means adapted to remove potentials due to muscular activity from said brain potentials, recognition means coupled to said filter means adapted to indicate the detection of brain potentials satisfying predetermined recognition parameters correlating to external epilepsy seizure symptoms, warning transmitter means coupled to said recognition means adapted to transmit an alarm signal when said brain potentials satisfy said recognition parameters, said recognition means being adapted to adjust said recognition parameters, said monitor means being further adapted to transmit said recognition parameters, and further comprising radio receiver means connected to said recognition means and adapted to receive an adjustment signal, and power supply means adapted to supply power to said filter means, recognition means and warning transmitter means; said external warning means comprising warning receiver means adapted to receive alarm signals from said warning transmitter means, alarm means adapted to notify the patient when alarm signals are received by said warning receiver means, program transceiver means comprising program transmitter means adapted to transmit said adjustment signal, adjustment means adapted to allow patient control of said adjustment signal, and program receiver means to receive said recognition parameters from said monitor means, and further comprising program display means adapted to display said recognition parameters.

4. The apparatus of claim 3 wherein said external warning means additionally includes counter means adapted to count the number of alarm signals received by said external warning means.

* * * * *